United States Patent [19]
Hazon et al.

[11] Patent Number: 5,139,484
[45] Date of Patent: Aug. 18, 1992

[54] AMBULATORY SYRINGE-PUSHER DEVICE FOR PARENTERAL INJECTIONS WITH OUTPUT SERVO-CONTROLLED BY THE CONTENTS OF THE SYRINGE

[75] Inventors: Bernard Hazon, 5, avenue de l'Opéra, 75001 Paris; André Sausse, deceased, late of Sceaux, by Frederic Sausse, heir; Jean-Claude Sausse, heir, Ceyrat, all of France

[73] Assignee: Bernard Hazon, Paris, France

[21] Appl. No.: 536,637

[22] PCT Filed: Jan. 7, 1988

[86] PCT No.: PCT/FR88/00012
 § 371 Date: Sep. 10, 1990
 § 102(e) Date: Sep. 10, 1990

[87] PCT Pub. No.: WO89/06145
 PCT Pub. Date: Jul. 13, 1989

[51] Int. Cl.[5] .......................... A61M 37/00
[52] U.S. Cl. ..................... 604/154; 604/155; 604/65; 128/DIG. 1
[58] Field of Search ............ 604/151, 152, 153, 154, 604/155, 65, 67; 128/DIG. 1, DIG. 12

[56] References Cited

U.S. PATENT DOCUMENTS

| 4,435,173 | 3/1984 | Siposs et al. | 604/155 |
|---|---|---|---|
| 4,662,872 | 5/1987 | Cane | 604/154 |
| 4,838,857 | 6/1989 | Strowe et al. | 128/DIG. 12 |
| 4,931,041 | 6/1990 | Faeser | 128/DIG. 1 |
| 4,952,205 | 8/1990 | Mauerer et al. | 604/154 |
| 4,976,696 | 12/1990 | Sanderson et al. | 604/154 |
| 5,034,004 | 7/1991 | Crankshaw | 604/154 |

FOREIGN PATENT DOCUMENTS

| 16343 | 10/1980 | European Pat. Off. . |
| 2809990 | 9/1978 | Fed. Rep. of Germany ... 128/DIG. 1 |

Primary Examiner—Gene Mancene
Assistant Examiner—Michael Lynch
Attorney, Agent, or Firm—Martin Lukacher

[57] ABSTRACT

This invention relates to a syringe-pusher device for ambulatory treatment, automatically delivering in a constant time compatible with the circadian rhythms, a fixed number of elementary volumes varying as a function of the prior filling volume of the syringe used by the operator. Said volume generally corresponding to the daily dose of drug can be directly read on the graduations on the syringe. A sound alarm is set off in the event of an impediment to the flow of the fluid as well as in the event of the untimely injection of elementary volume outside the set program.

20 Claims, 3 Drawing Sheets

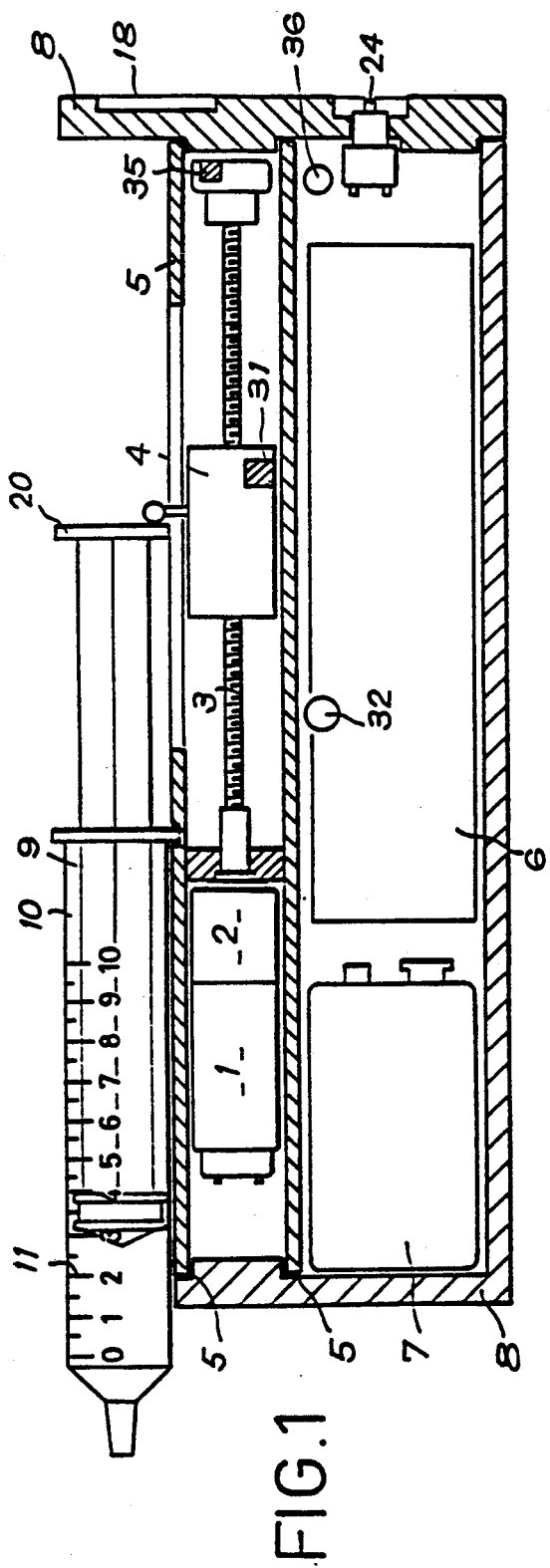

AMBULATORY SYRINGE-PUSHER DEVICE FOR PARENTERAL INJECTIONS WITH OUTPUT SERVO-CONTROLLED BY THE CONTENTS OF THE SYRINGE

FIELD OF THE INVENTION

The present invention relates to an ambulatory syringe-pusher device for parenteral injections whose output is servo-controlled by the contents of the syringe.

BACKGROUND OF THE INVENTION

Syringe-pusher devices according to the prior art generally employ an active means for translation of the piston of the syringe whose body is fixed on the apparatus.

Among such translation means, the one most often met with is a carriage and an endless screw actuated by an electric motor.

The motor which actuates the endless screw is either of the step-by-step or D.C. type. In the latter case, a reduction gear is generally placed between the motor and the endless screw.

For a geometrically defined syringe, the output of solution injected is directly proportional to the speed of translation of the piston-pusher member, said speed being in turn directly proportional to the angular rotation speed of the endless screw.

The angular speed of the endless screw may be adjusted in continuous rotation, for example by controlling the supply of the electric motor.

More recently, a discontinuous rotation of the endless screw has been preferred, by means of active periods separated by periods of relaxation. Elementary volumes or boluses are thus distributed during the active periods. A range of variation of the mean angular speed of the endless screw, and therefore of the mean output, which is much more extensive, for example from 1 to 100, is thereby obtained.

A programmer, generally a clock, initiates the rotation of the endless screw, which rotation terminates after description of a predetermined, constant angle.

A recent variant embodiment consists in replacing the programmation of the stop by a servo-control which stops the motor when the angle necessary and sufficient for delivering an elementary volume has been described. The variations in speed of the motor then have no influence on the volumetric precision of the elementary volume.

The output is adjusted by varying the frequency of the initiations of rotation of the endless screw, which is generally obtained by varying the duration of the relaxation insofar as the latter remains large compared with the duration of the active periods then considered as negligible.

These modes of adjustment of the speed of translation of the piston-pusher member present drawbacks.

In fact, the dosage generally being expressed in mols or units of active product per kilogram of body weight and per day, its translation into speed of translation of the piston of the syringe requires prior calculations. Generally, only one type of syringe can be used. Or it is necessary to employ conversion tables displaying the output as a function of the type of syringe used.

Moreover, the necessary durations of relaxation with low outputs obtained with syringes of too large relative capacity may be incompatible with the half-life of the drug injected and/or with the maintenance of the permeability of the intra-vascular injection means.

In addition, the time taken for the syringe to empty completely is variable, which renders the time table for renewing its content different from one patient to another.

Finally, the continuous operation of the motor is generally too slow to allow the rearward return of the carriage other than by disengaging said carriage and pushing it manually.

To make this type of syringe-pusher device, it may be constructed around a coaxial electro-mechanical assembly 1,2,3,4 contained in a closed envelope 5. Said electro-mechanical assembly 1,2,3,4 and the electronic control members 6 as well as the supply battery 7 may advantageously be placed in a casing 8 whose adequately formed expansions maintain the body of the syringe 9 by clamping, as in Patent PCT/FR87/00226 (FIG. 1).

BRIEF DESCRIPTION OF THE DRAWINGS

FIG. 1 is a sectional view illustrating the mechanical configuration of an ambulatory syringe-pusher device embodying the invention and showing a syringe mounted therein;

FIG. 2 is an end view from the left of the device shown in FIG. 1;

FIG. 3 is a schematic diagram illustrating the electrical system of the device shown in FIG. 1.

Figure 4:
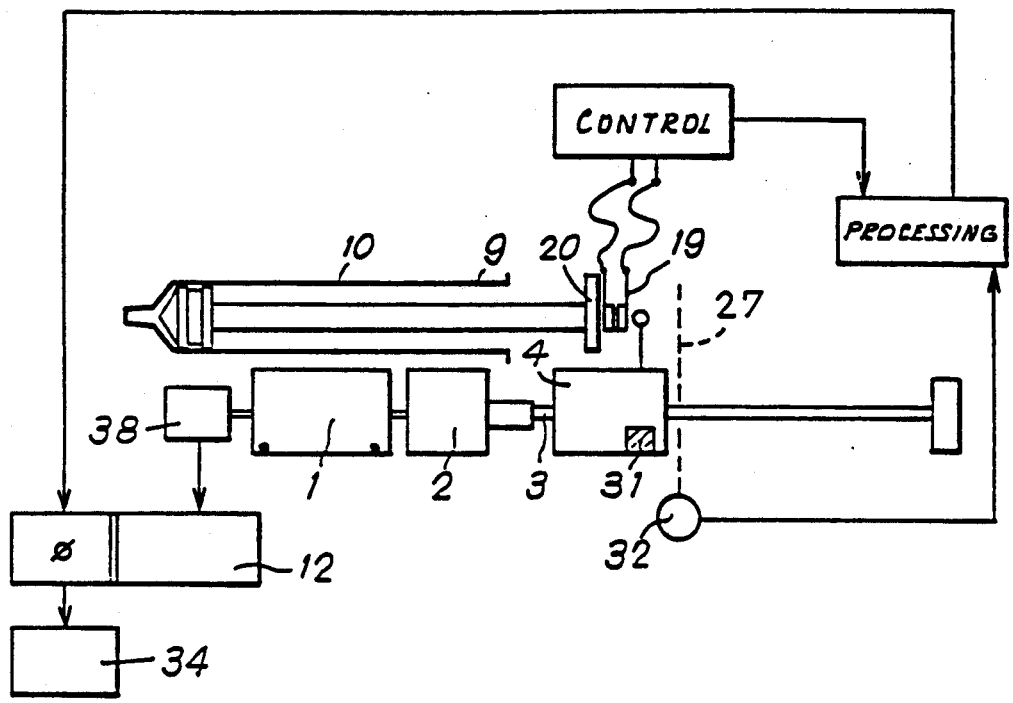
FIGS. 4, 5, 6 and 7 are schematic diagrams illustrating the device shown in FIGS. 1 and 3 in different positions during the operation thereof.

In the present invention, it has been found that the angle of rotation of the endless screw 3 corresponding to the delivery of an elementary volume must be proportional to the volume chosen for a determined duration of treatment and contained in a syringe 9 of sufficient nominal capacity for the desired independence in time.

The present invention describes a technique of automatic adjustment of the mean output which depends neither on the total duration of the injection, nor on the total number of elementary volumes, but solely on the volume of the elementary volume, i.e. the chosen volume initially introduced in a syringe 9 of any geometry.

In fact, the volume D of solution contained in a given syringe 9 has the form of a cylinder of variable height H and of constant base surface S.

Now, syringes generally bear on the cylinder 10 itself graduations 11 measuring the height H, but directly expressed in millilitres. The parameter S is therefore eliminated and the control of the mean output Q is reduced to the control of the mean speed V of translation of the height H defined for volume D, during the total time of emptying of the syringe 9.

The following may be expressed:

$$V = H/t$$

We have chosen to leave t constant whatever the volume D contained in the syringe 9. It is advantageously chosen to be equal to 24 hours or to a simple multiple or sub-multiple of this duration; in this way, the end of perfusion is foreseeable and may easily coincide with the rhythms of the patient and of the caring staff.

It is thus possible to vary D as a function of the titer of the solution of active product, of the weight of the patient or of his/her body surface, immediately and virtually without risk of error since D is displayed on the graduation scale 11 borne on the cylinder 10 of the syringe 9.

If the precision of the graduations 11 of the syringe 9 appeared insufficient, the syringe 9 might for example be weighed and the adequate value of H corresponding to the volume D chosen deduced therefrom.

This being so, and as mentioned in the state of the art, the half-life of the product injected as well as the maintenance of the permeability of the catheter do not allow too long durations of relaxation between two consecutive elementary volumes. Now, in general, said period of relaxation is only slightly different from t/n where n is the number of elementary volumes injected during time t. Experience has shown that the above requirements did not make it possible advantageously to use less than one hundred elementary volumes per 24 hours.

Control of the mean output Q being obtained by varying the volume of the elementary volume, it will suffice adequately to vary the elementary translation d corresponding to the delivery of said elementary volume so that $d = H/n$.

In order to render automatic the determination of the elementary translation $d = H/n$, the gear motor 1-2, coaxial endless screw 3 and piston-pusher member 4 assembly is used as intrinsic means for measuring the height H of the cylinder in the form of which the does D to be injected is contained in the syringe 9 placed in the syringe-holder of the device.

For the device to be informed of the instantaneous position of the piston-pusher member 4, a potentiometer may be used whose slide is fast with the piston-pusher member 4 or any other analog system.

In the embodiment described hereinbelow, the digital method has been preferably chosen, in non-limiting manner, which consists in counting the positive and negative revolutions of the endless screw 3 (FIG. 4).

Advantageously, these revolutions or fractions or revolution of the endless screw 3 are deduced from the revolutions or fractions of revolution of the motor 1 which drives it via a reduction gear 2 of known ratio. Said revolutions or fractions of revolution of the motor 1 are integrated in a reversible counter 12 shoe capacity corresponds to the whole possible mechanical stroke of the piston-pusher member 4. The revolutions are called negative in the direction of emptying of the syringe 9 and positive in the opposite direction. The signals counted in the reversible counter 12 correspond to revolutions or fractions of revolution of the motor 1. The may be obtained from a cam-contactor system 38, an optical system 38, or by means of a rotating magnet 38 acting remotely on an element sensitive to magnetism.

With a servo-motor 1 with low inertia, not free-running, with excitation by permanent magnet 13, the variations of the intensity passing through the armature 14 generated by short circuiting two consecutive blades of the collector 15 by the brushes 16, may preferably be collected. The variations in intensity will be collected at the terminals of a resistor 17 or inductance placed in series with the armature 14. Advantageously, the alternating component is separated, for example with a capacitor. The number of signals emitted per revolution of the motor is equal to the product of the odd number of blades 15 of the collector by the even number of brushes 16. The signals 38 are then shaped for example with a Schmidt trigger. The polarity of the signals also gives the direction of rotation of the motor (FIG. 3).

Advantageously and in non-limiting manner, the digital situation of the piston-pusher member 4 controlled by the reversible counter 12 is visualized by a display 18 of low consumption, for example a liquid crystal display which will have the further advantage of indicating by its extinction the generally cut-off of supply, for example upon activation of a safety circuit (FIG. 2). This same display may advantageously indicate on order the state of charge-discharge of the supply battery by visualization of the integration of the intensity received or supplied.

Figure 5:
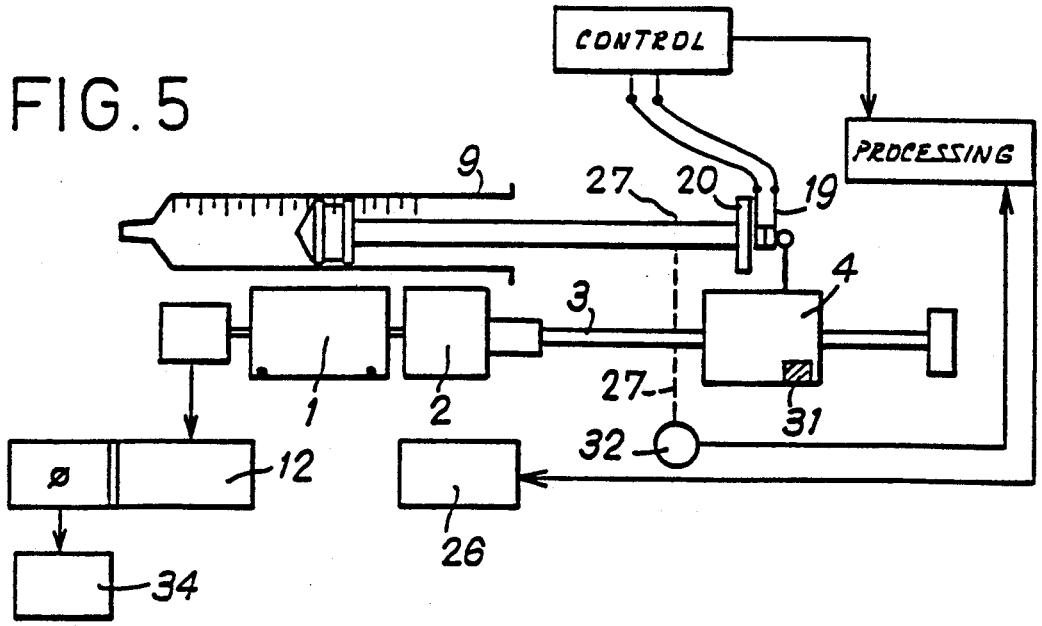

The position of the piston-pusher member 4 is recorded consecutively when the syringe 9 is totally empty, then when the syringe 9 is filled to the chosen volumetric dose. In both cases, the recordal of the instantaneous position of the piston-pusher member 4 is controlled by means 19 for detecting the physical contact of the piston-pusher member 4 and of the piston 20 of the syringe 9 (FIGS. 4 and 5). In order to determine the physical contact of the piston--usher member 4, and of piston 20, sensors of known design may be used. It is preferable to exploit the variation of the intensity of the current passing through the armature 14 of the motor 1. A voltage representative of said intensity may advantageously be collected at the terminals of the resistor 17 or inductance in series with the armature 14, and previously described.

The signals coming from the terminals of said resistor 17 or inductance are discrimated in amplitude and in frequency. Thus may be distinguished in variations of first order (21) or rapid waves function of the speed and direction of rotation of the motor already mentioned hereinabove and variations of second order (22) or slow waves corresponding to the variation of the value of the forces of friction (FIG. 3).

In fact, the intensity passing through the armature is proportional to the forces of friction off-load on the one hand, to which are added, upon physical contact of the piston-pusher 4, those of the piston 20 on the cylinder 10 of the syringe 9, as well as to the frictions of the solution in the flow tubes.

A third, maximum, order (23) of variations of said intensity appears when the pressure of the fluid contained in the syringe 9 becomes excessive further to an impediment to the flow of said fluid, for example by obturation or puckering of the injection tubes and/or thrombotic obturation of the catheter, or by mechanical impediment to the advance of the piston 20, particularly when it comes into abutment on the bottom of cylinder 10, or finally, by the appearance of an intravascular counter-pressure.

Every time the motor 1 starts in forward operation, the intensity peak corresponding to the kinetic energy of starting is eliminated with the aid of a delay time system acting on the waves of second (22) and third (23) order.

The operator has a fugitive manual control at his disposal for the continuous and rapid starting of the motor 1: forward (24), corresponding to the direction of emptying of the syringe 9 and reverse (25). Reverse operation can always be activated, even when the generally supply is interrupted. Forward operation makes it possible to obtain the physical contact of the piston-pusher member 4 and of the piston 20 in all the possible positions of said piston 20 within the maximum stroke. Said maximum stroke length is divided into two segments. One, at the front end of the mechanical stroke, is chosen so that the piston-pusher member 4 in physical contact with the piston 20 of an empty syringe 9 placed on the device, is always located in said front segment, whatever the design of syringe 9 chosen. In general, said front segment corresponds to one tenth of the maximum stroke, which advantageously limits the minimum volumetric dose 10 injectable to about one tenth of the nominal capacity of the syringe 9 (FIG. 4).

The passage over the boundary 27 between the front short segment and the rear long segment may for example be detected by means of a permanent magnet 31 fast with the piston-pusher member 4 acting remotely on a member 32 sensitive to magnetism.

The operations for measuring the height H of the dose D contained in the syringe 9 will now be described, these operations being considered as a calibration of the device prior to injection.

The operator places the totally empty syringe 9, piston 20 in abutment on the bottom of the cylinder 10, in the member for containing the device, after having, if necessary, withdrawn the piston-pusher member 4 by means of the manual reverse control 25.

He/she then displaces the piston-pusher member by means of the front manual control 24 until contact of the piston-pusher member 4 and the piston 20 of the syringe 9 is obtained. Such physical contact, which always occurs int eh short front segment, automatically controls the return-to-zero of the reversible counter 12, which return-to-zero provokes the general cut-off of the supply, with the exception of the manually controlled, rapid reverse operation (FIG. 4). The operator immediately returns the piston-pusher member 4 into the long rear segment at a sufficient distance to allow introduction of the syringe 9.

The syringe 9 is then filled to the chosen dose then replaced on the member containing the device. The operator then proceeds with the manual rapid forward operation of motor 1. When the physical contact of the piston-pusher member 4 and of piston 20 occurs, necessarily in the long rear segment, a bistable trigger circuit 26 passes from rest position to work position (FIG. 5). Said passage immediately and sequentially triggers off the following operations:

1. Stop of the supply of motor 1 via the continuous rapid advance.
2. Transfer of the reading of the reversible counter 12 previously divided by the product of the total number of elementary volumes n by a factor P function of the reduction ratio of the reduction gear 2 and of the number of signals 38 emitted per revolution or fractions of revolution of the motor 1, into the memory of a preconfigurable counter 29.
3. Closure of a circuit such that the signals to come from the rotation of motor 1 will subsequently be directed, parallel to the reversible counter 12, on the preconfigurable counter 29 previously and automatically returned to zero.
4. Closure of a circuit for measuring the antagonistic force exerted by the piston 20 on the piston-pusher member 4.
5. Initiation of the clock 28 whose task is to deliver the pulses for starting up motor 1.

Starting of the clock 28 consecutive to the triggering of the bistable trigger circuit 26 will initiate rotation of motor 1 after a time equal to the period of said clock 28.

Figure 6:
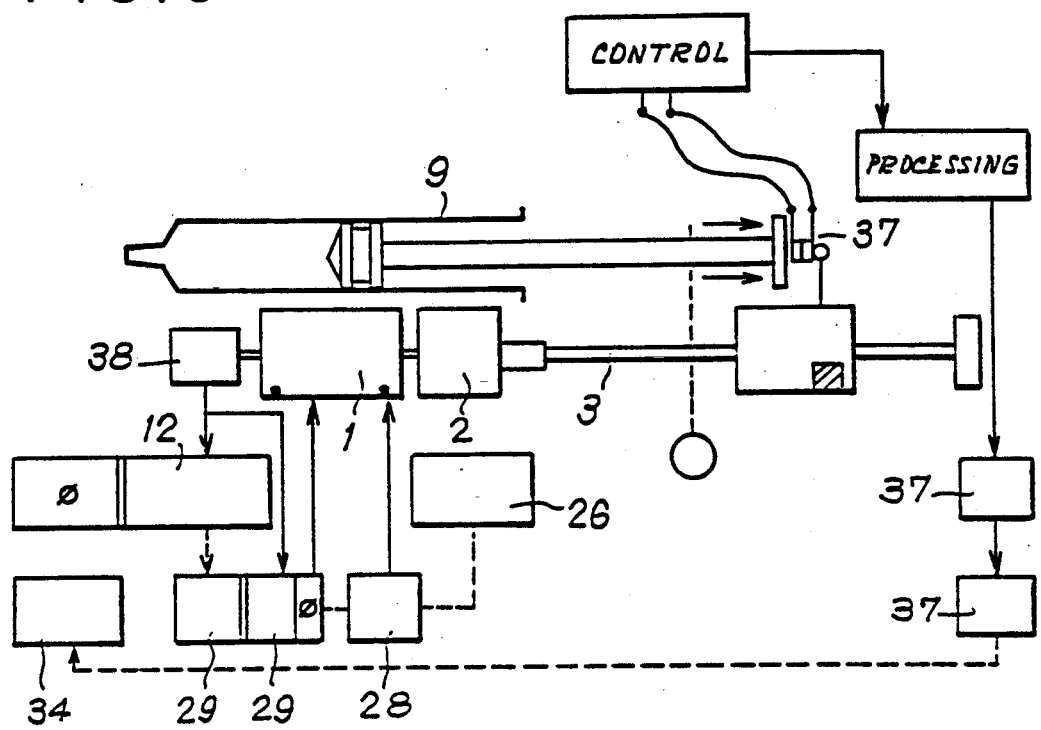
Figure 7:
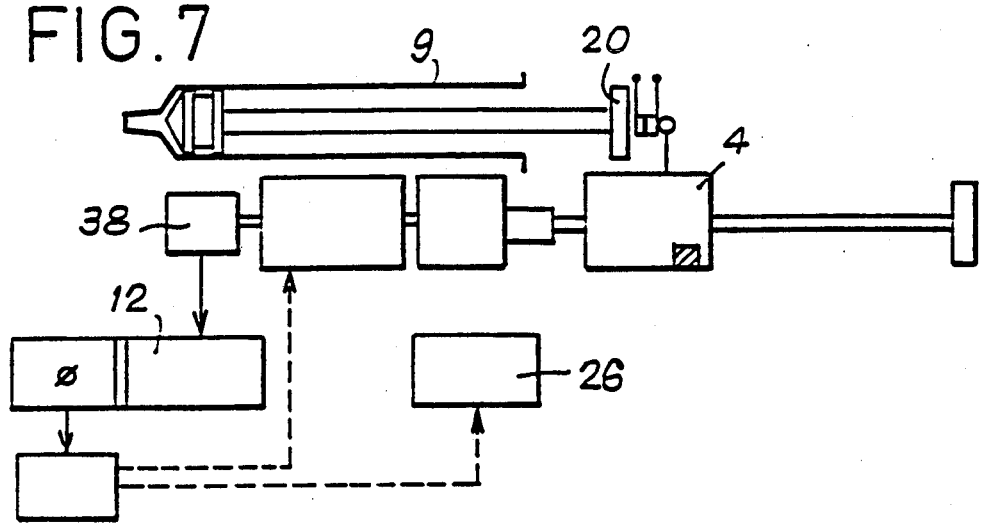

Stopping of said rotation of motor 1 with braking by short circuiting of the armature 14 is obtained when the count of the preconfigerable counter 29 coincides with the count transferred into its memory upon triggering of the bistable trigger circuit 26 in accordance with the modalities mentioned above (FIG. 6). The delivery of the elementary volumes then continues until the syringe 9 is completely empty (FIG. 7). The position of the piston-pusher member 4 then corresponds to the zero of the reversible counter 12, which provokes general cut-off of the supply 34, except for manual rapid reverse operation. This position is thus conserved indefinitely in memory and will make it possible subsequently to eliminate that part of the calibration corresponding to the empty syringe as long as the same type of syringe is used.

Two safety circuits with sound alarm are provided. The first (37) indicates the appearance of an excessive pressure and/or the stop of the translation of the piston 20. A mechanical impediment to the translation of the piston 20 provokes a sudden increase in the intensity passing through the armature 14, i.e. a variation of third order (23) as described hereinabove. With the bistable trigger circuit 26 in work position corresponding to normal injection, said variation of third order 23 triggers off a sound alarm. If the operator does not remove the obstacle, a delay time cuts off general supply after a period of the order of five minutes, which has for its effect to return the reversible counter 12 to zero. A general cut-off of the supply whilst the syringe 9 is not totally empty, indicates a posteriori the incident and the position of the piston 20 its time.

The second safety circuit affords protection from the immediately consecutive distribution of two elementary volumes of maximum volume without intermediate period of relaxation.

To that end, the rotation of the endless screw 3 is directly integrated in a special counter so that the angle of rotation corresponding to the delivery of said two elementary volumes immediately causes stoppage of the motor 1 by general and total cut-off of the supply and advantageously the excitation of a visual so-called danger display so as to prevent the apparatus from being switched on again.

With a judicious choice of the pitch of the endless screw, the maximum elementary volume can be delivered with less than one revolution of the endless screw 3. The distinct counter will consequently indicate any excess of an angle of rotation equal to two revolutions whenever operation of the clock 28 is initiated (FIG. 1).

If not, said counter will return to zero. Detection of the rotation of the endless screw may advantageously and in non-limiting manner be obtained by a magnet 35 fixed thereon and acting remotely on an element 36 sensitive to magnetism, as in Patent PCT/FR87/00226.

What is claimed is:

1. In a syringe-pusher device having a syringe for containing a volume of material therein for injection for ambulatory treatment, said device employing a coaxial D.C. motor, a reduction gear including an endless screw, an improved system for distributing a plurality of elementary volumes or boluses separated in time by periods of relaxation in response to the rotation of said screw which comprises means for operating said motor for providing an output corresponding only to the height of material of indifferentiated type introduced into said syringe prior to injection, and servo-control means responsive to said output for operating said motor at times separated by said periods to control the mean output of said material injected by said syringe.

2. The device of claim 1 wherein aid servo-control means includes means for automatic adjustment of the elementary volume proportionately to any volume introduced into the syringe of indifferentiated type prior to injection.

3. The device of claim 1 wherein said servo-control means includes automatic adjustment means responsive to the number of elementary volumes of constant volume proportionally to the volume introduced in the syringe of indifferentiated type prior to injection.

4. The device of claim 1 wherein aid syringe has a piston-pusher member operably connected to said endless screw, and said control means for said motor comprises a reversible counter which integrates the positive and negative revolutions of the motor.

5. The device according to claim 4 wherein said control means includes means for controlling the instantaneous position of the piston pusher member and comprises a potentiometer having a slide mechanically fast with said pusher member.

6. The device of claim 5 wherein the position of said piston-pusher member is calibrated and further comprising means for recording the positions of the piston pusher member when the syringe is completely empty, and then when the syringe is charged with the chosen volume, and the calibrated distance between these positions of the piston pusher member.

7. The device of claim 1 wherein aid syringe has a piston and a piston-pusher member extending therefrom, the maximum possible stroke of the piston-pusher member being divided into two unequal segments, said piston-pusher member being always disposed in the shorter of said segments when it is in physical contact with the piston of said syringe when completely empty.

8. The device of claim 1 wherein said motor operating means comprises a clock and means for initiation for rotation of the motor on the control of the clock, said motor having an armature and said piston-pusher displacement being calibrated from an initiation location, and means for controlling the stopping of the motor by short circuiting said armature comprising means for comparison of the number of revolutions described by the motor rom said initiation with the datum issued from the calibrated positions of said piston-pusher member.

9. The device of claim 8 wherein said means for controlling said stopping comprises means for the integration of the revolutions or fractions of revolution of the motor after every initiation of the clock is obtained, said integration means comprising a preconfigurable counter.

10. The device of claim 9 wherein said stopping control means comprises means for dividing the datum recorded form the counter during the calibration by the total number of elementary volumes and by a factor function of the reduction ratio of the reduction gear and of the revolutions of the motor to provide a count, and means for presetting the preconfigurable counter with said count.

11. The device of claim 1 wherein said motor has a collector with two consecutive blades which contact brushes, and means for the integration of the revolutions or fractions of revolution of said motor comprises means for short circuiting the two consecutive blades of the collector during its passage between one of the brushes to provide signals and integrating said signals.

12. The device of claim 11 further comprising a component which affects the passage of signals, and wherein the signals coming from the short circuiting means are collected at the terminals of the component, said motor having an armature in series with said inductor or resistor.

13. The device of claim 12 further comprising means responsive to the signals collected at the terminals of the inductor or the resistor for discriminating said signals in accordance with the polarity, frequency and amplitude thereof in at least three orders of response to the variation of the intensity of said signals appearing across said armature.

14. The device of claim 13 further comprising means for integrating the signals of first order in accordance with the polarity thereof for the entire duration of the calibration and injection operations of said device, said integrating means comprising a reversible counter.

15. The device of claim 14 further comprising a preconfigurable counter said reversible counter being responsive to signals of first order of one polarity during injection operations for presetting the preconfigurable counter.

16. The device of claim 15 wherein said piston-pusher controls a piston of said syringe and the stroke of said pusher has unequal front and rear segments over which it is displaced and further comprising means responsive to the signals of second order and of a polarity characteristic representing the physical contact of the piston-pusher and of the piston to provoke during calibration on the front short segment before return to zero of the reversible counter and immediately thereafter, the general cut off of operating voltage to said motor, and in the real long segment, the initiation of the injection operations.

17. The device of claim 16 wherein said device has a safety system providing a timed sound alarm, and further comprising means responsive to the signals of third order of one polarity to provoke the stoppage of said motor and the operation of said safety system.

18. The device of claim 1 wherein said control means comprises a clock and an integrator of the revolutions or fractions of revolution of the endless screw and mechanically fast therewith which counts the number of elementary volumes delivered further to every initiation of said motor by the clock.

19. The device of claim 18 wherein said control means includes means for the counting of two elementary volumes immediately consecutive to an initiation of the clock which irrevocably stops the motor and excites a permanent signal for placing the device out of service.

20. The device of claim 19 wherein the integrator of revolutions or fractions of revolution of the endless screw is formed by a permanent rotating magnet fixed mechanically at the end of the endless screw and acting remotely on an element sensitive to magnetism.

* * * * *